United States Patent [19]  [11] 4,212,190
Coover et al.  [45] Jul. 15, 1980

[54] ACOUSTICAL PARTICLE DETECTOR AND METHOD
[75] Inventors: Stephen R. Coover; Parker C. Reist, both of Chapel Hill, N.C.
[73] Assignee: Research Triangle Institute, Research Triangle Park, N.C.
[21] Appl. No.: 970,636
[22] Filed: Dec. 18, 1978
[51] Int. Cl.² ............................................. G01N 15/00
[52] U.S. Cl. ............................................. 73/28
[58] Field of Search ............................ 73/28, 432 PS
[56] References Cited
U.S. PATENT DOCUMENTS
3,434,335  3/1969  Langer ..................................... 73/28

Primary Examiner—S. Clement Swisher
Attorney, Agent, or Firm—B. B. Olive

[57] ABSTRACT

The capability for differentiating particles according to size is provided in an improved acoustical detection apparatus and method for detecting particulate matter in air or other gases. This is accomplished by controlling the flow of the gas through the capillary section of an acoustic sensor such that the flow conforms to a predetermined Reynolds number selected according to the particle size of interest. It has been found that acoustical sensors exhibit a threshold for particle size detection which varies with the Reynolds number of the flow of a gas through it. Thus, the detection of particles above a given size is achieved by controlling the flow parameters to yield a Reynolds number appropriate for detecting particles of such size.

17 Claims, 5 Drawing Figures

ACOUSTICAL PARTICLE DETECTOR AND METHOD

BACKGROUND OF THE INVENTION

1. Field of the Invention

The invention relates generally to the analysis of particles which are suspended in atmospheric air or other gases and more particularly to an acoustical method and apparatus for detecting, sizing and counting such particles.

2. Description of the Prior Art

It has been known for more than a decade that when airborne particles are passed at high velocities through a capillary tube and then suddenly projected into an expanded exit cavity, audible acoustical pulses are produced which, according to some authors, appear to be generated in the vicinity of the capillary exit. Each of the pulses so obtained is attributable to a single particle and consists of a decaying sinusoidal oscillation having a duration of from about 0.5 to 30 milliseconds depending upon the design and operational characteristics of the acoustical system employed.

Although the mechanism by which such audio pulses are produced has not yet been established, the possibility that the phenomenon might be used to size airborne particles has been investigated as evidenced by the report of G. Langer in the Journal of Colloid Science 20, 602–609 (1965).

Langer notes in this report that he applied the principle in the laboratory to count ice crystals in supercooled air streams and found that his sensor was capable of detecting particles down to 5 microns in size. He further notes that when an attempt was made to relate pulse amplitude to particle size, it was found that pulse amplitude was independent of particle size and density. Thus, pulse amplitude did not provide a means for screening particle size. Indeed, he states that "If the sensor could measure particle size, many other applications would be possible".

U.S. Pat. No. 3,434,335 was awarded to Langer for the device described above. The Acoustical Particle Detector and Method of the present invention uses a detecting unit similar to that of Langer but adds an important feature lacking in the Langer device directed to particle size differentiation by selection of the corresponding flow Reynolds number for the gas in the capillary section of the device.

In a subsequent study reported by Reist and Burgess in the March-April 1968 issue of the American Industrial Hygiene Association Journal, an experiment was conducted in which the same particle was repeatedly passed through an acoustic detector and it was found that the initial pulse amplitude would vary by more than 100% for a single particle. This finding was considered by the authors to present a major impediment to the use of this acoustic system for particle sizing.

A still further study on the application of the aforenoted acoustic phenomenon to the detection and counting of airborne particles is reported in a doctoral dissertation titled "Pulse Processing From Particle Detectors" by David R. Hemenway which was submitted to the Faculty of the University of North Carolina, Chapel Hill, North Carolina, in 1974 and is now on file in the library of that institution. This study was directed principally to improving the detection procedures of acoustical sensors.

From the foregoing, it is apparent that considerable attention has been given over the years to the development of a useful acoustical particle detector. However, despite these efforts and the progress resulting therefrom, the acoustical phenomenon has remained a laboratory curiosity. Practical application of the principle in the analysis of airborne particulate size has been restrained by the lack of a capability for differentiating particles on the basis of size. It is, therefore, a principal object of this invention to provide an acoustical method and apparatus for analyzing airborne particles wherein such particles can be both counted and sized.

SUMMARY OF THE INVENTION

According to the present invention, airborne or other aerosol particles are sized as they are caused to flow through an acoustical sensor by controlling such flow to correspond with a predetermined Reynolds number. By the term "aerosol" as used throughout the specification and in the appended claims there is meant a dispersed system consisting of a gas phase medium with a solid or liquid dispersed phase. This capability for differentiating aerosol particles according to size is based upon the discovery that the production of a pulse by such particles in an acoustic element is dependent upon a "critical" flow Reynolds number which varies linearly with particle diameter. In practice, this means that only particles whose diameter exceeds the threshold for a given flow Reynolds number will produce an acoustical pulse upon passage through an acoustical sensor under the flow conditions represented by said given Reynolds number and that particles whose diameter is less than the threshold for such flow as represented by the flow Reynolds number will pass through the sensor undetected.

In carrying out the procedure, a sample of the aerosol to be analyzed is passed through an acoustic sensor under conditions of flow which are consistent with a predetermined Reynolds number, which is selected in accordance with the particle size or sizes of interest. The acoustic pulses generated by each of such particles are detected and counted by an electronic system and circuitry which includes a blanking circuit for preventing the decaying sinusoidal pulse train from registering more than one pulse for a single particle as it passes through the sensor. From the total count, the number of particles above a selected size per unit volume of the gas can be ascertained by simple calculation.

DETAILED DESCRIPTION OF THE INVENTION

As is well known, the Reynolds number is a dimensionless quantity used in fluid mechanics to characterize flow regimes within conduits and may be defined by the expression:

$$Re = \frac{v \cdot d \cdot p}{n}$$

where v is the average velocity of a fluid of density p and viscosity n which is flowing in a circular conduit of diameter d.

Flow Reynolds numbers below 2300 are usually indicative of laminar flow, while values above 4000 are usually indicative of turbulent flow. A Reynolds number within the range between 2300 and 4000 is usually indicative of transistional flow, i.e., a flow that is oscillating between laminar and turbulent. However, these are not hard and fast rules and laminar flow can exist at a Reynolds number substantially above 4000 in a conduit having a very smooth internal surface and which is free of obstructions, e.g., laminar flows have been achieved in certain specially designed wind tunnels at a flow Reynolds number of 40,000. Nevertheless, laminar flows at a Reynolds number in excess of 4000 should be called "superlaminar" as only slight perturbations are required to cause transition to turbulent flow.

The basic principles of the invention and the manner and means by which it may be practiced will be best understood by reference to the accompany drawings.

Figure 1:
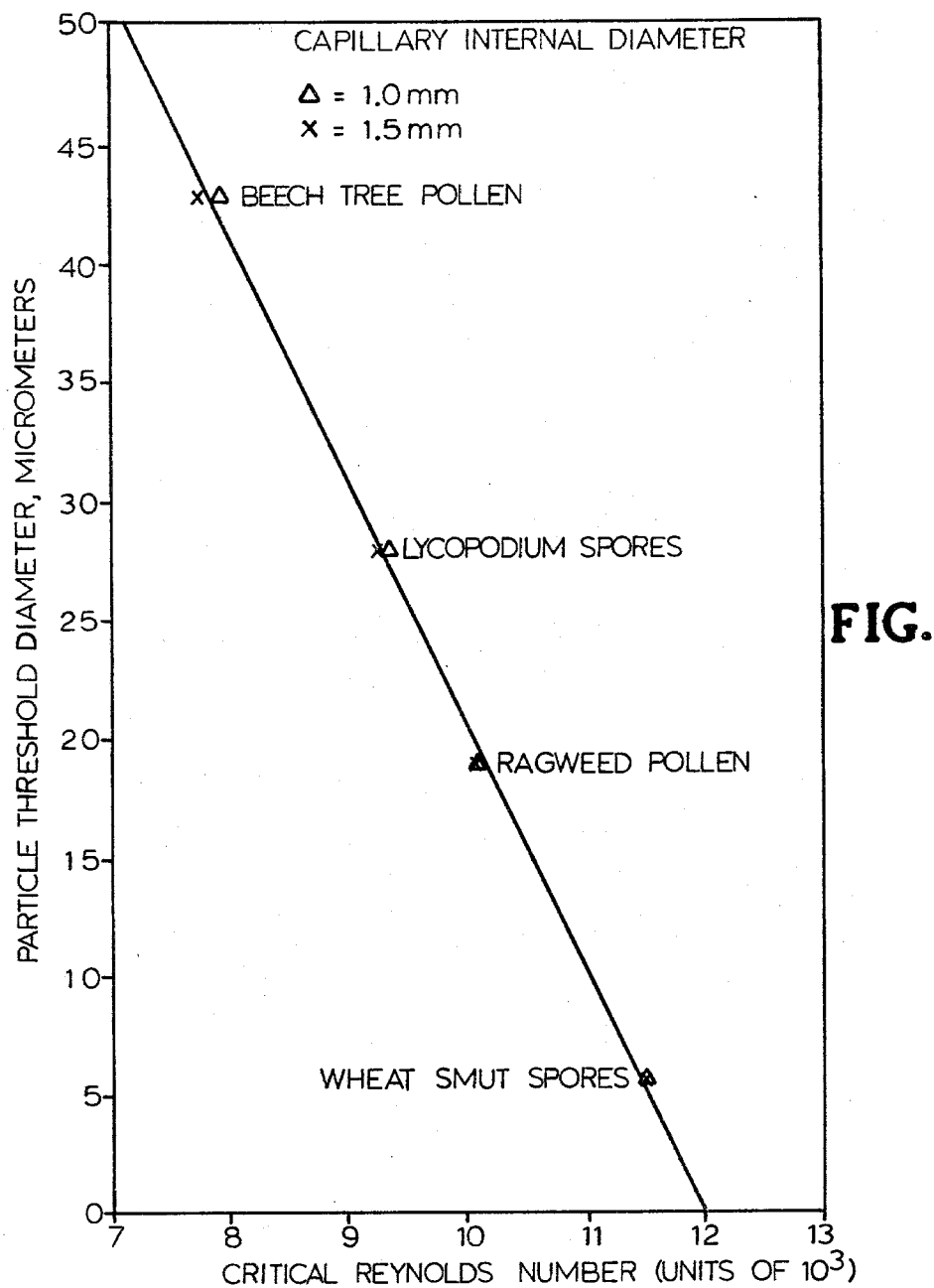
FIG. 1 is a graphical representation of test data wherein particle threshold diameter is plotted against the observed "critical" Reynolds number for detection.

Referring initially to FIG. 1, it is seen from this graphical representation of data obtained from tests on airborne particles of various sizes that the acoustical sensor exhibits a threshold for particle-size detection which varies with the Reynolds number of the flow of air through the capillary section of the sensor. Also, as the plotted data show, the relationship between threshold particle diameter and "critical" Reynolds number is linear and independent of the sensor's capillary tube diameter.

By the term "critical" Reynolds number there is meant the minimum flow Reynolds number for which a particle of a given diameter will generate a detectable pulse as it passes through the acoustic sensor. Thus, if the Reynolds number of a gas flow which contains the particle is equal to or greater than the "critical" value for such size particle a detectable pulse for that particle will be produced. On the other hand, if the Reynolds number of the gas flow is less than the "critical" value, the particle will pass through the sensor undetected.

The term "particle threshold diameter", as used in the graph of FIG. 1, may be defined as a particle having the minimum diameter which will permit detection by the acoustic sensor at a given flow Reynolds number through the sensor.

An integral particle size distribution may be obtained in accordance with the present invention by determining the particle counts per unit volume of gas at different flow Reynolds numbers to enable detection of particles having different threshold sizes. The flow Reynolds number is readily altered by appropriate adjustments in the rate of flow of the gas through the capillary section of the acoustical element. As an alternative, a plurality of acoustical elements having capillary tubes with selective differences in diameter may be used at the same gas flow rate to obtain the desired variation in the flow Reynolds number.

Figure 2:
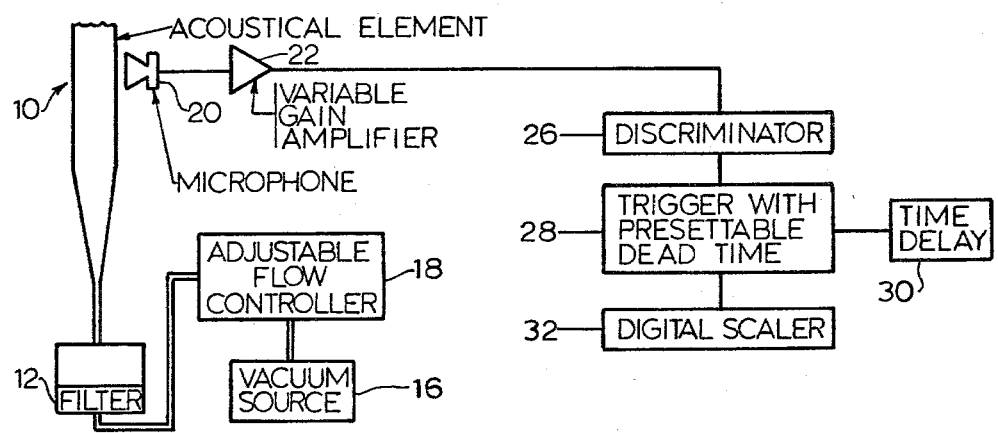
FIG. 2 shows an apparatus for carrying out the invention in block diagram.

Attention is now directed to FIG. 2 where an apparatus for carrying out the invention is illustrated in block diagram. The apparatus includes an acoustical element 10 through which a gaseous atmosphere, which contains minute particles to be sized and counted, is passed. The particle containing gas under test is drawn through the acoustical element 10 by means of a vacuum pump or other vacuum source 16, which is operatively connected to the exit of the acoustical element. Such gas flow could also be accomplished by the application of a positive pressure, e.g., by positioning a positive displacement pump at the entrance of the acoustical element. However, as a practical matter, the use of a vacuum system to create the required pressure differential across the acoustical element is generally preferred. An adjustable flow meter 18 calibrated in terms of flow rate and minimum detectable particle diameter is provided to control gas flow through acoustical element 10 in conformance with the desired flow Reynolds number.

The acoustical pulses generated by the particles as they pass through the acoustical element are detected and processed for counting by a system of circuitry which includes a microphone 20, a variable gain amplifier 22, a discriminator 26, a trigger 28 equipped with a presettable time delay 30, and a digital scaler 32. In operation, the acoustical pulses are detected by microphone 20 and amplified by the variable gain amplifier 22 before being applied to discriminator 26, which distinguishes between acoustical pulses and background "noise". The output from the discriminator is applied to trigger circuit 28 with the dead time being pre-set to prevent multiple triggering from a single acoustical pulse generated by the passage of a particle through the acoustical element of the sensing device. The output of trigger circuit 28 is, in turn, fed to digital scaler 32 for numerical display.

Figures 3, 3A:
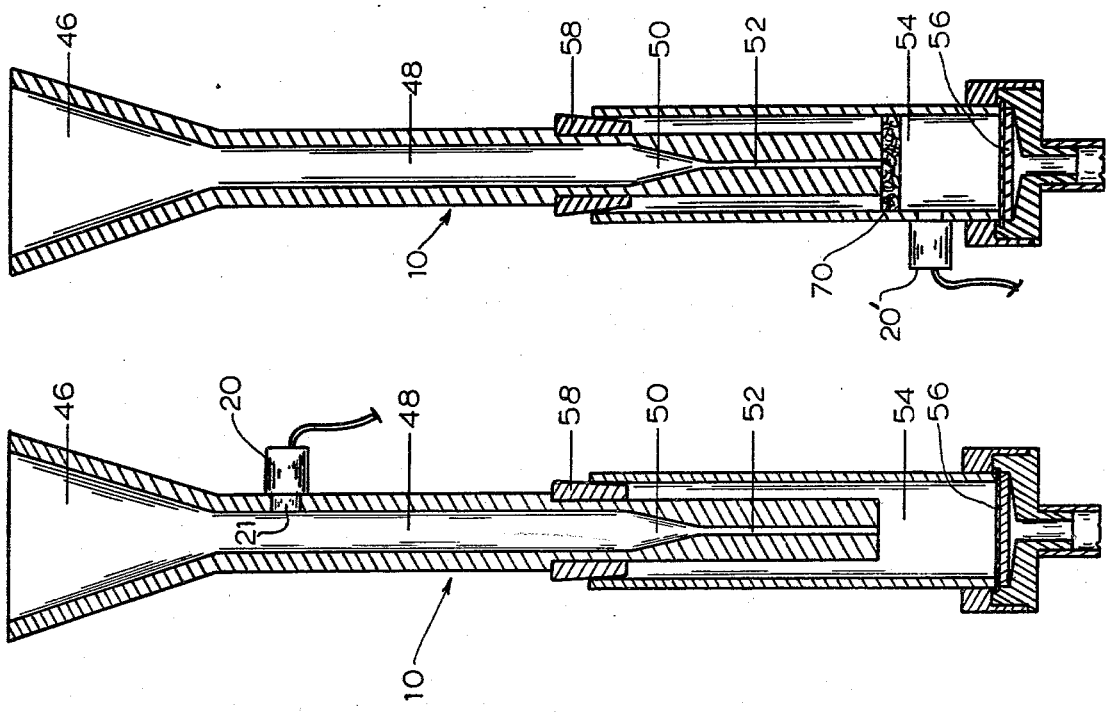
FIG. 3 illustrates the design features of one form and FIG. 3A of another form of acoustical element according to the invention.

Reference is next made to FIG. 3 of the drawings where the design features of one embodiment of an acoustical element suitable for use in practicing the present invention are illustrated. As shown, the acoustical element designated generally by the numeral 10 includes a gas entry section consisting of a funnel-shaped structure 46 at its forward end attached to a straight hollow gas inlet tube 48 which has a substantially constant diameter throughout its length. The microphone 20 of the pulse sensing system is mounted proximate to aperture 21 on inlet tube 48 so as to be in communication with the hollow interior thereof from where the sound signals generated by the sensing device may be detected.

Beneath and contiguous with hollow tube 48 is a linear frusto-conical section 50 which tapers into a smooth walled capillary restriction 52. The capillary, in turn, exits into expansion chamber 54. In order to protect the downstream vacuum pump and flow control means from becoming inoperative due to the particles passing through acoustical element 10, a filter 56 is placed in the exit section of the expansion chamber 54. Filter 56 also serves to muffle any sound emanating from the vacuum pump or other suction producing means.

As shown, the expansion chamber 54 is a separate element into which the balance of the components which constitute the acoustical element can be inserted and withdrawn, with a soft rubber flange 58 serving to seal the connection between the parts when the device is in operation. However, it should be understood that the expansion chamber could be made integral with the other components.

The funnel-shaped structure 46 at the forward end of gas inlet tube 48 is merely optional and not an essential component of the acoustical element. The length of the gas inlet tube 48 is not critical and can vary widely. However, it is desirable that a length be chosen which will permit the microphone 20 to be positioned a sufficient distance from capillary restriction 52 to reduce interference from background noise. Also, when the unit is operated in open air, a longer inlet tube gives the turbulence a chance to moderate before the air enters the capillary section 52 of the sensor.

The acoustical element may be fabricated from any material which will provide smooth internal walls when formed into a passageway for a gaseous atmosphere, such as air. One such substance is glass. Likewise, metal or plastic may be used so long as smooth laminar transition of the gaseous atmosphere is made possible as it enters the device. Although the dimensions of the various parts of the acoustical element are subject to some variation, it is desirable that the internal diameter of the capillary 52 be in the range of from about 1 to 4 mm with the length being in the range of from about 4 to 7 cm. The frustoconical section 50 exhibits an internal taper of preferably about 5° half-angle.

Figure 4:
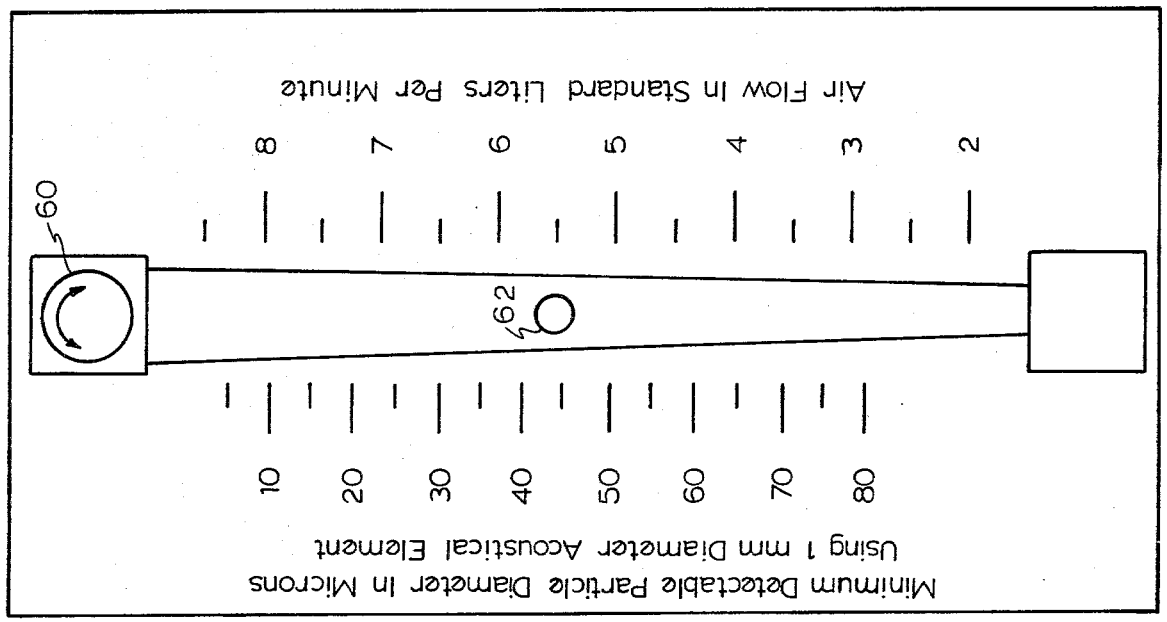
FIG. 4 illustrates a flow metering device suitable for use with the apparatus of this invention.

In order to control the flow rate of the gaseous atmosphere under test through the acoustical element to achieve the appropriate flow Reynolds number, a gas metering device, such as a rotameter, is interposed in the vacuum line. A control panel especially adapted for use with such gas metering device in carrying out the procedure of this invention is illustrated in FIG. 4. A knob 60 is provided for controlling the valve of a rotameter or other flow control device with float bob 62 serving as an indicator for reading the appropriate scale values. It will be noted that the air flow is calibrated in terms of minimum detectable particle diameter. Thus, referring to the scales shown in the drawing, this means, for example, that when the air flow is 8 standard liters per minute, the minimum detectable particle diameter is 10 microns. In other words, the actual "critical" flow Reynolds number in such instance corresponds to a particle threshold diameter of 10 microns.

FIG. 3A of the drawings illustrates an alternative embodiment of the acoustical element 10 in which microphone 20' is situated below capillary restriction 52. To reduce the noise due to turbulence at the exit of element 10, a noise filter comprising a wad of fiberglass 70 is inserted at the position shown in FIG. 3A. At this position, the pulse is extremely short with no ringing as in the case with the microphone above the capillary as in FIG. 3. This means that a much higher counting rate can be tolerated. From the sign of the pulse, it appears that the pulse is the result of a momentary pressure drop in the exit area when the laminar flow in the capillary tube is momentarily disrupted by the passage of a particle. In other words, microphone 20' is acting as a pressure transducer. However, the data associated with FIGS. 1 and 4 still pertain.

While fiberglass material has been found suitable for purposes of noise filter 70, other fibrous air transmitting materials can readily be found that will produce equivalent results.

From the foregoing description, it will be appreciated that the present invention provides means by which the particles contained in a representative sample of a gaseous atmosphere can be both discriminated on the basis of size and counted. This dual capability is important in many applications.

We claim:

1. An acoustical method for detecting particles in an aerosol which are above a given size, said method comprising:

(a) providing an acoustical element adapted for allowing audio pulses to be generated by aerosol particles when the aerosol is passed therethrough at high velocities and wherein said acoustical element consists essentially of a conically-shaped entry section which tapers into a capillary tube which in turn exits into an expansion chamber;
    (b) establishing a pressure differential across said acoustical element to cause the flow of a representative sample of said aerosol therethrough;
    (c) maintaining the flow of said aerosol sample through said acoustical element by means enabling the Reynolds number to be adjusted and with said means adjusted in accordance with a preselected Reynolds number, with said Reynolds number being selected according to the particle size range of interest and the ability of said particles within said size range to generate an acoustic pulse under the flow conditions represented by said Reynolds number; and
    (d) detecting the acoustic pulses generated by said particles.

2. The method according to claim 1, wherein said pressure differential across said acoustical element is established by pulling a vacuum within said acoustical element.

3. The method according to claim 1, wherein said pressure differential across said acoustical element is established by the application of a positive pressure to the aerosol sample being passed therethrough.

4. The method according to claim 1, wherein the gas phase of said aerosol consists of atmospheric air.

5. The method according to claim 1 wherein said detecting is accomplished by utilizing a microphone positioned proximate and below the exit end of said capillary tube and an air transmitting noise filter at said exit end effective to reduce turbulence thereat.

6. The method according to claim 4 wherein the dispersed phase of said aerosol contains pollen particles.

7. An acoustical method for analyzing an aerosol to determine the number of particles above a given size present therein, said method comprising:

(a) providing an acoustical element adapted for allowing audio pulses to be generated by aerosol particles when the aerosol is passed therethrough at high velocities and wherein said acoustical element consists essentially of a conically-shaped entry section which tapers into a capillary tube which in turn exits into an expansion chamber;
    (b) establishing a pressure differential across said acoustical element to cause the flow of a representative sample of said aerosol therethrough;
    (c) maintaining the flow of said aerosol sample through said acoustical element by means enabling the Reynolds number to be adjusted and with said means adjusted in correspondence with a preselected Reynolds number with said Reynolds number being selected according to the particle size range of interest and the ability of said particles within said size range to generate an acoustic pulse under the flow conditions represented by said Reynolds number;
    (d) detecting the acoustic pulses generated by said particles;
    (e) counting said detected acoustic pulses; and
    (f) relating said count to the number of said particles per unit volume of said aerosol.

8. The method according to claim 7 wherein the gas phase of said aerosol consists of atmospheric air.

9. The method according to claim 8 wherein the dispersed phase of said aerosol contains pollen particles.

10. The method in accordance with claim 7 wherein an integral particle size distribution is obtained by conducting a series of test runs with said preselected Reynolds number being changed in each of said test runs.

11. The method according to claim 10 wherein said Reynolds number is changed by changing the flow rate of said aerosol through said acoustical element.

12. The method according to claim 10 wherein said Reynolds number is changed by changing the diameter of the capillary tube of said acoustical element.

13. An apparatus for detecting and deriving a count of particles of given size per unit volume in a sample of gas, comprising:
 (a) means for establishing a flow of said gas;
 (b) an acoustical element including an interconnected gas inlet tube, a frusto-conical entry chamber, capillary tube and expansion chamber in the path of said flow enabling audio pulses to be generated within said element by high velocity particles drawn through said entry chamber into said tube and expansion chamber by the effect of said flow;
 (c) gas metering means for controlling the rate of said gas flow through the capillary of said acoustical element, and wherein the rate of said metered flow is calibrated against minimum detectable particle diameter;
 (d) a microphone positioned proximate an aperture formed in said acoustical element and communicating with said path of flow for detecting said audio pulses; and
 (e) circuit means connected to said microphone for processing and separating said pulses and producing counting signals therefrom and including means to display said count for determining the number of particles above a given diameter per unit volume of said gas according to said metered gas flow.

14. An apparatus as claimed in claim 13 wherein said means for establishing said flow comprises a vacuum source.

15. An apparatus as claimed in claim 13 wherein said means for establishing said flow comprises a positive pressure source.

16. An apparatus as claimed in claim 13 wherein said aperture formed in said acoustical element comprises an aperture formed in said entry chamber.

17. An apparatus as claimed in claim 13 wherein said aperture formed in said acoustical element comprises an aperture formed in said expansion chamber and including air transmitting noise filter means at the exit end of said capillary tube effective to reduce turbulence thereat.

* * * * *